US009931359B2

(12) United States Patent
Fuchs et al.

(10) Patent No.: US 9,931,359 B2
(45) Date of Patent: Apr. 3, 2018

(54) METHODS AND COMPOSITIONS FOR INFUSION OF TRANSIENTLY ENGRAFTING, SELECTED POPULATIONS OF ALLOGENEIC LYMPHOCYTES TO TREAT CANCER

(71) Applicant: The Johns Hopkins University, Baltimore, MD (US)

(72) Inventors: Ephraim Joseph Fuchs, Owings Mills, MD (US); Heather Jill Symons, Annapolis, MD (US); Lode Swinnen, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 170 days.

(21) Appl. No.: 14/398,724

(22) PCT Filed: Mar. 15, 2013

(86) PCT No.: PCT/US2013/032129
§ 371 (c)(1),
(2) Date: Nov. 3, 2014

(87) PCT Pub. No.: WO2013/169386
PCT Pub. Date: Nov. 14, 2013

(65) Prior Publication Data
US 2015/0132290 A1 May 14, 2015

Related U.S. Application Data

(60) Provisional application No. 61/644,126, filed on May 8, 2012.

(51) Int. Cl.
| | |
|---|---|
| *A61K 35/28* | (2015.01) |
| *A61K 35/26* | (2015.01) |
| *A61K 45/00* | (2006.01) |
| *A61K 35/17* | (2015.01) |
| *C12N 5/00* | (2006.01) |
| *A61K 31/664* | (2006.01) |
| *A61K 45/06* | (2006.01) |
| *C12N 5/0783* | (2010.01) |

(52) U.S. Cl.
CPC ............ *A61K 35/17* (2013.01); *A61K 31/664* (2013.01); *A61K 45/06* (2013.01); *C12N 5/0087* (2013.01); *C12N 5/0638* (2013.01)

(58) Field of Classification Search
None
See application file for complete search history.

(56) References Cited

U.S. PATENT DOCUMENTS

| | | |
|---|---|---|
| 7,361,332 B2 | 4/2008 | Granger et al. |
| 2001/0006631 A1 | 7/2001 | Hiserodt et al. |
| 2007/0128629 A1 | 6/2007 | Hildebrand et al. |

OTHER PUBLICATIONS

Alyea et al., "CD8+ Cell Depletion of Donor Lymphocyte Infusions Using CD8 Monoclonal Antibody-Coated High Density Microparticles (CD8-HDM) after Allogeneic Hematopoietic Stem Cell Transplantation: A Pilot Study," *Bone Marrow Transplant.* (2004), 34:123-128, Nature Publishing Group.

Ciurea et al., "Donor-Specific Anti-HLA Abs and Graft Failure in Matched Unrelated Donor Hematopoietic Stem Cell Transplantation," *Blood* (2011), 118(22):5957-5964, The American Society of Hematology.

Dazzi and Goldman, "Adoptive Immunotherapy Following Allegeneic Bone Marrow Transplantation," *Annu. Rev. Med.* (1998), 49:329-340, Annual Reviews Inc.

Giralt et al., "CD8-Depleted Donor Lymphocyte Infusion as Treatment for Relapsed Chronic Myelogenous Leukemia after Allogeneic Bone Marrow Transplantation," *Blood* (1995), 86(11):4337-4343, The American Society of Hematology.

Lee et al., "The Feasibility and Clinical Efficacy of In Vivo Adsorption of Isohemagglutinins with Fresh Frozen Plasma (FFP) Infusion in Major ABO-Incompatible Allogeneic Stem Cell Transplantation," *Korean J. Hematol.* (2005) 40(4):254-260.

Xie et al., "Naïve Tumor-Specific $CD4^+T$ Cells Differentiated In Vivo Eradicate Established Melanoma," *J. Exp. Med.* (2010), 207(3):651-667, The Rockefeller University Press.

Alyea, E.P. et al.: "*Toxicity and efficacy of defined doses of CD4(+) donor lymphocytes for treatment of relapse after allogeneic bone marrow transplant*"; Blood, vol. 91, No. 10, May 15, 1998, pp. 3671-3680.

Luznik, L. et al: "*HLA-Haploidentical Bone Marrow Transplantation for Hematologic Malignancies Using Nonmyeloablative Conditioning and High-Dose, Posttransplantation Cyclophosphamide*"; Biol Blood Marrow Transplant, vol. 14, No. 6, Jun. 1, 2008, pp. 641-650.

Munchel, Ashley T. et al.: "*Treatment of hematological malignancies with nonmyeloablative, HLA-haploidentical bone marrow transplantation and high dose, post-transplantation cyclophosphamide*"; Best Practice & Research Clinical Haematology, vol. 24, No. 3 , 2011, pp. 359-368.

(Continued)

*Primary Examiner* — Michail Belyavskyi
(74) *Attorney, Agent, or Firm* — DLA Piper LLP (US)

(57) ABSTRACT

The invention provides methods and compositions for administration of allogeneic lymphocytes as an exogenous source of CD4+ T cell help for endogenous, tumor-reactive CD8+ T cells. Depletion of CD8+ T cells from the donor lymphocyte infusion reduces the risk of sustained engraftment and graft-versus-host disease. Removal of regulatory T cells from the infused population may augment the ability of non-regulatory T cells to provide help for endogenous effectors of anti-tumor immunity. Allogeneic T cell therapy is typically given in the context of allogeneic stem cell transplantation, in which the patient receives highly immunosuppressive conditioning followed by an infusion of a stem cell graft containing unselected populations of mature T cells. In the treatment described here, the graft is engineered to minimize the possibility of sustained donor cell engraftment, and the anti-tumor effector T cells derive from the host.

15 Claims, 3 Drawing Sheets

(56) References Cited

OTHER PUBLICATIONS

Symons, H. J. et al.: "*The Allogeneic Effect Revisited: Exogenous Help for Endogenous, Tumor-Specific T Cells*"; Biology of Blood and Marrow Transplantation, vol. 14, No. 5, May 1, 2008, pp. 499-509.

Extended European Search Report dated Oct. 6, 2015, regarding EP 13 788 469.8.

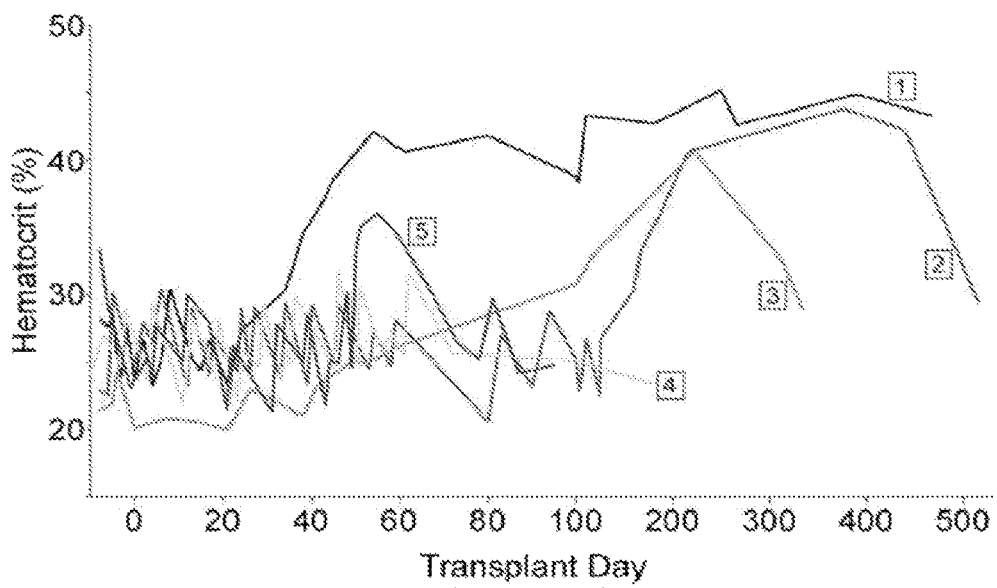

Figure 1. Hematocrit values in MDS patients experiencing graft rejection following non-myeloablative conditioning and transplantation of marrow from partially HLA-mismatched relatives.

FIG. 1

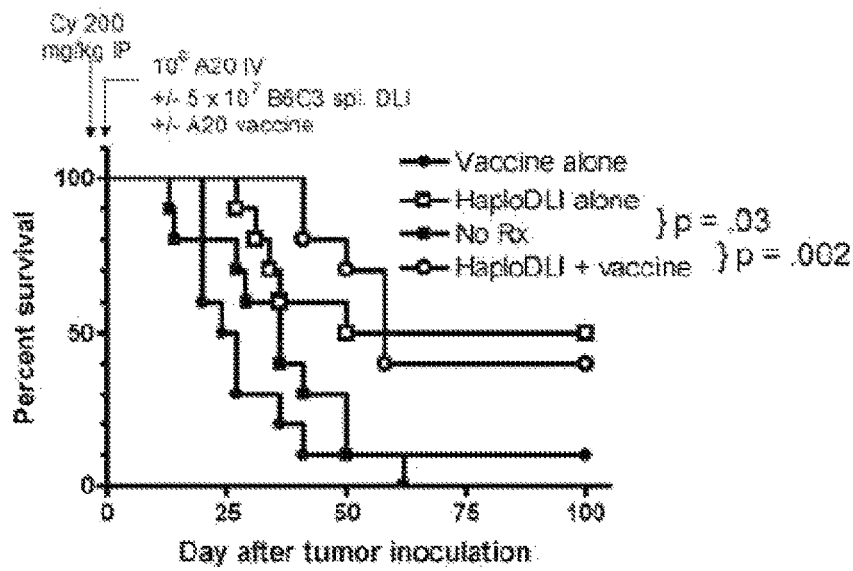

Figure 2. Non-engrafting DLI induces anti-tumor immunity. BALB/c x C57BL/6 F1 mice (H-2$^{b/d}$; n=10/group) were conditioned with Cy 200 mg/kg IP on day −1. On day 0, they received 10$^6$ A20 lymphoma cells IV +/− 5 x 10$^7$ spleen cells from partially MHC-mismatched B6 x C3H F1 donors (H-2$^{b/k}$) +/− autologous tumor cell vaccine sc (10$^6$ irradiated A20 + 2 x 10$^5$ irr. B78H1-GM-CSF).

FIG. 2

METHODS AND COMPOSITIONS FOR INFUSION OF TRANSIENTLY ENGRAFTING, SELECTED POPULATIONS OF ALLOGENEIC LYMPHOCYTES TO TREAT CANCER

CROSS-REFERENCE TO RELATED APPLICATIONS

This application is a 35 USC § 371 National Stage application of International Application No. PCT/US2013/032129 filed Mar. 15, 2013, now pending; which claims the benefit under 35 USC § 119(e) to U.S. Application Ser. No. 61/207,627 filed May 26, 2010. The disclosure of each of the prior applications is considered part of and is incorporated by reference in the disclosure of this application.

GRANT INFORMATION

This invention was made with government support under Grant Nos. IR01 CA105148-01 and P01 CA15396 awarded by the National Institutes of Health. The government has certain rights in the invention.

BACKGROUND OF THE INVENTION

Field of the Invention

The invention relates generally to immunology and more specifically, to methods and compositions containing allogeneic lymphocytes to treat cancer.

Background Information

The immune system of a host provides the means for quickly and specifically mounting a protective response to pathogenic microorganisms and also for contributing to rejection of malignant tumors. Immune responses have been generally described as including humoral responses, in which antibodies specific for antigens are produced by differentiated B lymphocytes, and cell mediated responses, in which various types of T lymphocytes eliminate antigens by a variety of mechanisms. For example, CD4 (also called CD4+) helper T cells that are capable of recognizing specific antigens may respond by releasing soluble mediators such as cytokines to recruit additional cells of the immune system to participate in an immune response. CD8 (also called CD8+) cytotoxic T cells are also capable of recognizing specific antigens and may bind to and destroy or damage an antigen-bearing cell or particle. In particular, cell mediated immune responses that include a cytotoxic T lymphocyte (CTL) response can be important for elimination of tumor cells and cells infected by a microorganism, such as virus, bacteria, or parasite.

Cancer includes a broad range of diseases and affects approximately one in four individuals worldwide. A CTL response is a key feature of effective cancer vaccines; effective CD4 T cell help is also likely to play a critical role in productive CD8 T cell activation and thus provide clinical benefit.

With respect to microbial infections, malaria, tuberculosis, HIV-AIDS and other viral infections such as Herpes Simplex Virus (HSV) infections (the leading cause of genital ulcers worldwide) continue to contribute to global health concerns. HSV-2 prevalence is increasing at an alarming rate across the globe. In the United States, the overall HSV-2 sero prevalence rate exceeds 20%, and in developing nations HSV-2 prevalence is estimated between 30% and 50%. In addition to the profound burden of HSV-2 infection in adults, the incidence of neonatal HSV-2 infection is increasing. Even when treated, neonatal encephalitis from HSV-2 infection has a mortality >15%, and the neurological morbidity among HSV-2 infected infants is an additional 30 to 50% of surviving cases. Concomitant with the HSV-2 epidemic is a stark realization that HSV-2 infection substantially increases the risk for HIV-1 acquisition and transmission. Data from Africa show that HSV-2 infection can increase the risk for HIV transmission by as much as 7-fold and that as many as half of newly acquired HIV cases are directly attributed to HSV-2 infection. Overall, the relative risk of HIV acquisition increases more than 2-fold in HSV-2-infected individuals.

Emerging evidence suggests that cancers induce a state of unresponsiveness in lymphocytes that are specific for antigens uniquely expressed by the cancer. However, this unresponsiveness should be able to be reversed. Several human tumors are infiltrated by CD8+ T cells, and the degree of CD8+ T cell infiltration often correlates with absence of metastases and improved survival. However, these CD8+ T cells may not eliminate the cancer because of functional paralysis of tumor-specific CD4+ T cells.

SUMMARY OF THE INVENTION

The present invention is based on the seminal discovery that infusion of allogeneic lymphocytes containing CD4+ T cells can break tolerance in host anti-tumor CD8+ T cells, even though the donor cells do not engraft long term in the recipient. Administration of chemotherapy prior to the allogeneic cell infusion can augment the anti-tumor effect of the transiently engrafting lymphocytes, by promoting homeostatic expansion of the transferred lymphocytes, and/or by depleting host regulatory T cells and myeloid-derived suppressor cells. The immune response to cancer is hampered by functional defects of the patient's CD4+ T cells. Infusions of allogeneic lymphocytes can provide an exogenous source of CD4+ T cell help for endogenous, tumor-reactive CD8+ T cells. Depletion of CD8+ T cells from the donor lymphocyte infusion reduces the risk of sustained engraftment and graft-versus-host disease. Removal of regulatory T cells from the infused population may augment the ability of non-regulatory T cells to provide help for endogenous effectors of anti-tumor immunity.

Allogeneic T cell therapy is typically given in the context of allogeneic stem cell transplantation, in which the patient receives highly immunosuppressive conditioning followed by an infusion of a stem cell graft containing unselected populations of mature T cells. The goal of alloSCT is to obtain sustained engraftment of the donor cells and entails the risk of mortality from graft-versus-host disease. In the treatment described here, the graft is engineered to minimize the possibility of sustained donor cell engraftment, and the anti-tumor effector T cells derive from the host. Thus the therapy entails a unique cooperation of host and donor lymphocytes during the period of transient donor cell engraftment.

This is a treatment that can be applied to any human or animal cancer. Variations of the present invention include: 1) variations of the chemotherapy regimen that is given prior to infusion of allogeneic lymphocytes (may include cyclophosphamide, 5-fluorouracil, gemcitabine, dasatinib, combinations thereof; 2) variations in the source of donor lymphocytes (may be from related or unrelated donors, may include defined mismatches at HLA Class I or Class II genetic loci; 3) variations in the types of cells selected for infusion, such as depletion of CD4+CD25+ regulatory T cells, depletion of CD8+ T cells. Donors may be immunized to defined antigens prior to lymphocyte infusions or may be polarized with cytokines ex vivo to enrich for Type I (IFN-gamma producing) or Type 17 (IL-17-producing) T cells.

In a first embodiment, the invention provides A method of making an allogenic lymphocyte composition comprising: providing a peripheral blood cell composition from a human donor allogenic to the recipient, the peripheral blood cell composition comprising CD4+ T-cells, CD8+ T-cells, and natural killer cells, wherein (i) the donor comprises at least one human leukocyte antigen (HLA) Class II allele mismatch relative to the recipient in the donor versus the recipient direction and the HLA Class II allele mismatch is at a gene selected from the group consisting of HLA-DRB1, HLA-DQB1, and HLA-DPB1, and (ii) the recipient does not have detectable antibodies reactive against human leukocyte antigens of the donor; and making the allogenic lymphocyte composition from the peripheral blood cell composition by reducing the number of CD8+ T-cells in the peripheral blood cell composition by at least one order of magnitude, wherein (a) the number of CD4+ T-cells in the allogenic lymphocyte composition differs from the number of CD4+ T-cells in the peripheral blood cell composition by less than about 50%, and (b) the number of natural killer cells in the allogenic lymphocyte composition is less than or equal to the number of natural killer cells in the peripheral blood cell composition, with the proviso that the CD4+ T-cells of the allogenic lymphocyte composition are not activated ex vivo.

In another embodiment, the invention provides a composition made by the invention method. In yet another embodiment, the invention provides An allogenic human lymphocyte composition comprising: CD4+ T-cells and natural killer cells from the peripheral blood cell composition of a donor, wherein (i) the donor comprises at least one human leukocyte antigen (HLA) Class II allele mismatch relative to the recipient in the donor versus the recipient direction and the HLA Class II allele mismatch is at a gene selected from the group consisting of HLA-DRB1, HLA-DQB1, and HLA-DPB1, (ii) the recipient does not have detectable antibodies reactive against human leukocyte antigens of the donor, (iii) the number of CD4+ T-cells in the allogenic lymphocyte composition differs from the number of CD4+ T-cells in the peripheral blood cell composition by less than about 50%, (iv) the number of donor CD4+ T-cells based on an ideal body weight of the recipient in kilograms (kg) is between about $1\times10^5$ CD4+ T-cells/kg and about $1\times10^9$ CD4+ T-cells/kg, (v) the number of natural killer cells in the allogenic lymphocyte composition is less than or equal to the number of natural killer cells in the peripheral blood cell composition, and (vi) the allogenic lymphocyte composition has at least one order of magnitude fewer CD8+ T-cells relative to the peripheral blood cell composition; with the proviso that the CD4+ T-cells of the allogenic lymphocyte composition are not activated ex vivo.

The invention also provides a method of treating a disease or condition in a human subject, comprising: administering a lymphoreductive non-lymphoablative treatment to the subject to induce transient lymphopenia in the subject; and subsequently administering to the subject a first allogenic lymphocyte composition derived from a peripheral blood cell composition of a human, allogenic donor, the first allogenic lymphocyte composition comprising a number of CD4+ T-cells and a number of natural killer cells from the peripheral blood cell composition of the donor, wherein (i) the donor comprises at least one human leukocyte antigen (HLA) Class II allele mismatch relative to the subject in the donor versus the subject direction and the HLA Class II allele mismatch is at a gene selected from the group consisting of HLA-DRB1, HLA-DQB1, and HLA-DPB1, (ii) the subject does not have detectable antibodies reactive against human leukocyte antigens of the donor, (iii) the number of CD4+ T-cells in the first allogenic lymphocyte composition differs from the number of CD4+ T-cells in the peripheral blood cell composition by less than about 50%, (iv) the number of donor CD4+ T-cells based on an ideal body weight of the subject in kilograms (kg) is between about $1\times10^5$ CD4+ T-cells/kg and about $1\times10^9$ CD4+ T-cells/kg, (v) the number of natural killer cells in the first allogenic lymphocyte composition is less than or equal to the number of natural killer cells in the peripheral blood cell composition, and (vi) the first allogenic lymphocyte composition has at least one order of magnitude fewer CD8+ T-cells relative to the peripheral blood cell composition, with the proviso that the CD4+ T-cells of the first allogenic lymphocyte composition are not activated ex vivo.

In one aspect, subsequent to administering the first allogenic lymphocyte composition to the subject, the method further comprises administering a successive lymphoreductive non-lymphoablative treatment to the subject to induce transient lymphopenia in the subject; and subsequently administering to the subject a successive allogenic lymphocyte composition derived from an additional peripheral blood cell composition of an additional human, allogenic donor, the successive allogenic lymphocyte composition comprising a number of CD4+ T-cells and a number of natural killer cells from the additional peripheral blood cell composition of the additional donor, wherein (i) the additional donor comprises at least one human leukocyte antigen (HLA) Class II allele mismatch relative to the subject in the additional donor versus the subject direction and the HLA Class II allele mismatch is at a gene selected from the group consisting of HLA-DRB1, HLA-DQB1, and HLA-DPB1, (ii) the subject does not have detectable antibodies reactive against human leukocyte antigens of the additional donor, (iii) the number of CD4+ T-cells in the successive allogenic lymphocyte composition differs from the number of CD4+ T-cells in the additional peripheral blood cell composition by less than about 50%, (iv) the number of additional donor CD4+ T-cells based on an ideal body weight of the subject in kilograms (kg) is between about $1\times10^5$ CD4+ T-cells/kg and about $1\times10^9$ CD4+ T-cells/kg, (v) the number of natural killer cells in the successive allogenic lymphocyte composition is less than or equal to the number of natural killer cells in the additional peripheral blood cell composition, and (vi) the successive allogenic lymphocyte composition has at least one order of magnitude fewer CD8+ T-cells relative to the additional peripheral blood cell composition.

The invention also provides a method of making an allogenic lymphocyte composition for administration to a human recipient, comprising: providing a peripheral blood cell composition from a human donor allogenic to the recipient, the peripheral blood cell composition comprising a number of CD4+ T-cells, a number of CD8+ T-cells, and a number of natural killer cells, wherein (i) the donor has CD4+ T-cell immunity against an antigen present in the recipient, (ii) the donor comprises at least one human leukocyte antigen (HLA) Class II allele match relative to the recipient and the HLA Class II allele match is at a gene selected from the group consisting of HLA-DRB1, HLA-DQB1, and HLA-DPB1, and (iii) the recipient does not have detectable antibodies reactive against human leukocyte antigens of the donor; and making the allogenic lymphocyte composition from the peripheral blood cell composition by reducing the number of CD8+ T-cells in the peripheral blood cell composition by at least one order of magnitude, wherein (a) the number of CD4+ T-cells in the allogenic lymphocyte composition differs from the number of CD4+ T-cells in the peripheral blood cell composition by less than about 50%, and (b) the number of natural killer cells in the allogenic lymphocyte composition is less than or equal to the number of natural killer cells in the peripheral blood cell composition, with the proviso that the CD4+ T-cells of the allogenic lymphocyte composition are not activated ex vivo.

In another embodiment, the invention provides an allogenic lymphocyte composition derived from a peripheral blood cell composition of a human, allogenic donor for administration to a human recipient, the allogenic lymphocyte composition comprising: a number of CD4+ T-cells and a number of natural killer cells from the peripheral blood cell composition of the donor, wherein (i) the donor has CD4+ T-cell immunity against an antigen present in the recipient, (ii) the donor comprises at least one human leukocyte antigen (HLA) Class II allele match relative to the recipient and the HLA Class II allele match is at a gene selected from the group consisting of HLA-DRB1, HLA-DQB1, and HLA-DPB1, (iii) the recipient does not have detectable antibodies reactive against human leukocyte antigens of the donor, (iv) the number of CD4+ T-cells in the allogenic lymphocyte composition differs from the number of CD4+ T-cells in the peripheral blood cell composition by less than about 50%, (v) the number of donor CD4+ T-cells based on an ideal body weight of the recipient in kilograms (kg) is between about $1\times10^5$ CD4+ T-cells/kg and about $1\times10^9$ CD4+ T-cells/kg, (vi) the number of natural killer cells in the allogenic lymphocyte composition is less than or equal to the number of natural killer cells in the peripheral blood cell composition, and (vii) the allogenic lymphocyte composition has at least one order of magnitude fewer CD8+ T-cells relative to the peripheral blood cell composition; with the proviso that the CD4+ T-cells of the allogenic lymphocyte composition are not activated ex vivo.

The invention also provides an allogenic lymphocyte composition derived from a peripheral blood cell composition of a human, allogenic donor for administration to a human recipient, the allogenic lymphocyte composition comprising: a number of CD4+ T-cells and a number of natural killer cells from the peripheral blood cell composition of the donor, wherein (i) the donor has CD4+ T-cell immunity against an antigen not present in the recipient, (ii) the donor comprises at least one human leukocyte antigen (HLA) Class II allele match relative to the recipient and the HLA Class II allele match is at a gene selected from the group consisting of HLA-DRB1, HLA-DQB1, and HLA-DPB1, (iii) the recipient does not have detectable antibodies reactive against human leukocyte antigens of the donor, (iv) the number of CD4+ T-cells in the allogenic lymphocyte composition differs from the number of CD4+ T-cells in the peripheral blood cell composition by less than about 50%, (v) the number of donor CD4+ T-cells based on an ideal body weight of the recipient in kilograms (kg) is between about $1\times10^5$ CD4+ T-cells/kg and about $1\times10^9$ CD4+ T-cells/kg, (vi) the number of natural killer cells in the allogenic lymphocyte composition is less than or equal to the number of natural killer cells in the peripheral blood cell composition, and (vii) the allogenic lymphocyte composition has at least one order of magnitude fewer CD8+ T-cells relative to the peripheral blood cell composition; with the proviso that the CD4+ T-cells of the allogenic lymphocyte composition are not activated ex vivo.

In one embodiment, the invention provides a kit for use in treating a disease or condition in a subject, the kit comprising: a lymphocyte composition wherein the subject is the human recipient; and a nanoparticle composition comprising nanoparticles comprising the antigen not present in the human recipient.

Further, there is a method of treating a disease or condition in a human subject, comprising: administering to the subject an allogenic lymphocyte composition derived from a peripheral blood cell composition of a human, allogenic donor, the allogenic lymphocyte composition comprising a number of CD4+ T-cells and a number of natural killer cells from the peripheral blood cell composition of the donor, wherein (i) the donor has CD4+ T-cell immunity against an antigen present in the subject, (ii) the donor comprises at least one human leukocyte antigen (HLA) Class II allele match relative to the subject and the HLA Class II allele match is at a gene selected from the group consisting of HLA-DRB1, HLA-DQB1, and HLA-DPB1, (iii) the subject does not have detectable antibodies reactive against human leukocyte antigens of the donor, (iv) the number of CD4+ T-cells in the allogenic lymphocyte composition differs from the number of CD4+ T-cells in the peripheral blood cell composition by less than about 50%, (v) the number of donor CD4+ T-cells based on an ideal body weight of the subject in kilograms (kg) is between about $1\times10^5$ CD4+ T-cells/kg and about $1\times10^9$ CD4+ T-cells/kg, (vi) the number of natural killer cells in the allogenic lymphocyte composition is less than or equal to the number of natural killer cells in the peripheral blood cell composition, and (vii) the allogenic lymphocyte composition has at least one order of magnitude fewer CD8+ T-cells relative to the peripheral blood cell composition; with the proviso that the CD4+ T-cells of the allogenic lymphocyte composition are not activated ex vivo.

In one aspect, the invention provides a method of treating a disease or condition in a human subject, comprising injecting a nanoparticle composition into a tumor, wherein the nanoparticle composition comprises nanoparticles comprising an antigen not present in the subject, thus introducing the antigen into the subject; administering to the subject an allogenic lymphocyte composition derived from a peripheral blood cell composition of a human, allogenic donor, the allogenic lymphocyte composition comprising a number of CD4+ T-cells and a number of natural killer cells from the peripheral blood cell composition of the donor, wherein (i) the donor has CD4+ T-cell immunity against the antigen, (ii) the donor comprises at least one human leukocyte antigen (HLA) Class II allele match relative to the subject and the HLA Class II allele match is at a gene selected from the group consisting of HLA-DRB1, HLA-DQB1, and HLA-DPB1, (iii) the subject does not have detectable antibodies reactive against human leukocyte antigens of the donor, (iv) the number of CD4+ T-cells in the allogenic lymphocyte composition differs from the number of CD4+ T-cells in the peripheral blood cell composition by less than about 50%, (v) the number of donor CD4+ T-cells based on an ideal body weight of the subject in kilograms (kg) is between about $1\times10^5$ CD4+ T-cells/kg and about $1\times10^9$ CD4+ T-cells/kg, (vi) the number of natural killer cells in the allogenic lymphocyte composition is less than or equal to the number of natural killer cells in the peripheral blood cell composition, and (vii) the allogenic lymphocyte composition has at least one order of magnitude fewer CD8+ T-cells relative to the peripheral blood cell composition; with the proviso that the CD4+ T-cells of the allogenic lymphocyte composition are not activated ex vivo.

BRIEF DESCRIPTION OF THE DRAWINGS

FIG. 1 shows the hematocrits of the same five patients after BMT, with the jagged portions reflecting the effect of transfusion (graph).

FIG. 2 shows non-engrafting DLI induces anti-tumor immunity (graph).

DETAILED DESCRIPTION OF THE INVENTION

Figure 3A:
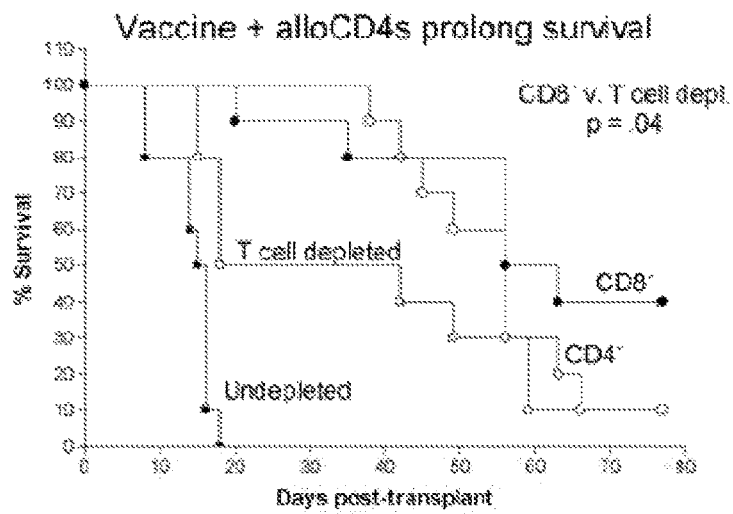
FIG. 3a shows engraftment of donor cells as vaccine plus alloCD4s prolong survival (graph).

The present disclosure arises at least in part from the seminal discovery that the immune response to cancer is hampered by functional defects of the patient's CD4+ T cells. Infusions of allogeneic lymphocytes can provide an exogenous source of CD4+ T cell help for endogenous, tumor-reactive CD8+ T cells. Depletion of CD8+ T cells from the donor lymphocyte infusion reduces the risk of sustained engraftment and graft-versus-host disease. Removal of regulatory T cells from the infused population may augment the ability of non-regulatory T cells to provide help for endogenous effectors of anti-tumor immunity. Allogeneic T cell therapy is typically given in the context of allogeneic stem cell transplantation, in which the patient receives highly immunosuppressive conditioning followed by an infusion of a stem cell graft containing unselected populations of mature T cells. In the treatment described here, the graft is engineered to minimize the possibility of sustained donor cell engraftment, and the anti-tumor effector T cells derive from the host. Thus, the therapy entails a unique cooperation of host and donor lymphocytes during the period of transient donor cell engraftment.

In one embodiment, the invention provides a method of making an allogenic lymphocyte composition for administration to a human recipient, preferably, the donor and recipient are not the same human. The method includes providing a peripheral blood cell composition from a human donor allogenic to the recipient, the peripheral blood cell composition comprising a number of CD4+ T-cells, a number of CD8+ T-cells, and a number of natural killer cells, some natural killer cells have CD8+ antigen and may be removed by the "reducing" step; however, preferred lymphocyte compositions of the present invention comprise at least some natural killer cells from the donor. In one aspect, (i) the donor comprises at least one human leukocyte antigen (HLA) Class II allele mismatch relative to the recipient in the donor versus the recipient direction (an HLA Class II allele mismatch in the donor versus recipient direction, i.e., "graft-versus-host direction) and the HLA Class II allele mismatch is at a gene such as HLA-DRB1, HLA-DQB1, or HLA-DPB1. The recipient does not have detectable antibodies reactive against human leukocyte antigens of the donor ("detectable antibodies" in this context are defined using standard methods of making this determination (for example, the recipient does not have antibodies against donor HLA molecules that are detectable by complement-dependent cytotoxicity, in flow cytometric cross-match assays a positive result is undesirable, or mean fluorescence intensity (MFI) of 3000 or greater in a solid phase immunoassay is unacceptable).

The allogenic lymphocyte composition is made from the peripheral blood cell composition by reducing the number of CD8+ T-cells in the peripheral blood cell composition by at least one order of magnitude, wherein (a) the number of CD4+ T-cells in the allogenic lymphocyte composition differs from the number of CD4+ T-cells in the peripheral blood cell composition by less than about 50%. In a preferred embodiment the ratio of the number of CD4+/the number of CD8+ T cells in the lymphocyte composition is preferably greater than or equal to about 30. Examples of some embodiments include, but are not limited to, the following doses per kilogram of recipient ideal body weight: a lymphocyte composition comprising 105 CD4+ cells typically has no greater than $3.2\times10^3$ CD8+ cells, $10^6$ CD4+ cells typically has no greater than $3.2\times10^4$ CD8+ cells, $10^7$ CD4+ cells typically has no greater than $3.2\times10^5$ CD8+ cells, $10^8$ CD4+ cells typically has no greater than $3.2\times10^6$ CD8+ cells, and $5\times10^8$ CD4+ cells typically has no greater than $1.6\times10^7$ CD8+ cells.

The number of natural killer cells in the allogenic lymphocyte composition is less than or equal to the number of natural killer cells in the peripheral blood cell composition, with the proviso that the CD4+ T-cells of the allogenic lymphocyte composition are not activated ex vivo. reduced by one order of magnitude, preferably about two orders of magnitude, more preferably to about five orders of magnitude. In one embodiment, the number of CD8+ cells is reduced by about 2.5 orders of magnitude (e.g., using the magnetic bead cell sorter method).

In one aspect, wherein if the donor and recipient are ABO blood type incompatible and the peripheral blood cell composition comprises a number of red blood cells, then making the allogenic lymphocyte composition further comprises reducing the number red blood cells. "ABO blood type incompatible," as used herein, refers to when the recipient has a major ABO red blood cell incompatibility against the donor, e.g., the recipient is blood type O and the donor is blood type A, B, or AB, the recipient is type A and the donor is type B or AB, or the recipient is type B and the donor is type A or AB.

In one aspect, the number of red blood cells comprises less than or equal to about 50 ml in packed volume. e.g., less than or equal to about 50 ml in packed volume, preferably less than or equal to about 30 ml in packed volume, further "packed volume" should be defined, for example, centrifugation of the lymphocyte composition would result is a packed volume of 50 ml or less of red blood cells; a measured volume sample of the lymphocyte composition could also be screened to provide a proportionally representative volume of packed blood cells.

In one aspect, the number of CD4+ T-cells in the allogenic lymphocyte composition differs from the number of CD4+ T-cells in the peripheral blood cell composition by less than about 20%. In some embodiments, the CD4+ T-cells are less than about 50%, less than about 40%, preferably less than about 20%, more preferably less than about 10%. In some embodiments, ex vivo expansion of CD4+ T-cells may be performed, in such embodiments the number of CD4+ T-cells can greatly exceed the original number. Such expansion is an alternative embodiment.

In some embodiments, CD4+ T-cells obtained from the donor are not intentionally expanded or intentionally differentiated ex vivo. Intentionally expanded or intentionally differentiated is distinguished from expansion or differentiation of the CD4+ T-cells that is merely a side effect (not intentional, inadvertent) of the method, for example, CD4+ T-cells can sometimes undergo differentiation by coming into contact with plastic, other examples of such inadvertent events. In another embodiment, there is a further proviso that stem cells have not been mobilized in the peripheral blood cell composition donor who is allogenic to the recipient.

In some aspects, reducing the CD8+ T-cells in the peripheral blood cell composition comprises using an anti-CD8+ antibody associated with magnetic particles or an anti-CD8+ antibody plus complement. The peripheral blood cell composition can be a whole blood product or an apheresis product, for example. Further, the HLA Class II allele mismatch in the donor versus the recipient direction can be a mismatch at HLA-DRB1. This limitation with an HLA Class II allele mismatch in the donor versus recipient direction is for example "graft-versus-host direction", wherein the at least one HLA Class II allele(s) mismatch in the direction of the allogenic donor versus the recipient further comprises the same HLA Class II allele(s) mismatch between the allogenic donor versus one or more first degree relatives of the recipient, which is desirable to preserve the opportunity for bone marrow transplantation from the first degree relatives to the recipient; ideally, all of the mismatches between donor versus recipient do not exist between a potential family bone marrow donor versus the recipient.

In some aspects, screening for one or more selection characteristic(s) is done and the screening is carried out on a subject selected from the group consisting the recipient, the donor, and one or more potential allogenic donor(s). For example, a selection characteristic is screening for serological reactivity to an infectious agent antigen. An infectious agent antigen is selected from the group consisting of a Human Immunodeficiency Virus (HIV) antigen, a Hepatitis Virus antigen, and a Cytomegalovirus antigen. Important agents to be screened for include, for example, HIV-1 antigen(s), HIV-2 antigen(s), hepatitis A virus antigen(s), hepatitis B virus antigen(s), hepatitis C virus antigen(s), CMV antigens, infectious diseases, etc. If the virus or infectious agent or an antigen thereof is the target of the therapy, one would not rule out a donor having the desired CD4+ mediated immune response against that agent.

In one aspect, the infectious agent antigen is a Cytomegalovirus antigen, the recipient and the donor are screened, and there is no serological reactivity to the Cytomegalovirus antigen in the recipient or the donor. In one aspect, the viral antigen is an influenza antigen and the influenza antigen is a hemagglutinin antigen or a neuraminidase antigen.

In another aspect, a selection characteristic is screening for more than one HLA Class II alleles. In certain instances, a potential allogenic donor is selected based on maximizing mismatch between the potential allogenic donor versus the recipient, in the potential allogenic donor versus recipient direction, at the more than one HLA Class II alleles, and the potential allogenic donor is chosen as the donor. In certain instances, a selection characteristic is screening for one or more HLA Class I allele(s).

A potential allogenic donor can be selected based on minimizing mismatch between the potential allogenic donor and the recipient at the more than one HLA Class I allele(s), and the potential allogenic donor is chosen as the donor.

In one embodiment, the invention provides an allogenic lymphocyte composition for administration to a human recipient obtained by the method of the invention as described herein.

If the recipient is seropositive for the CMV antigen, then the status of the donor does not matter. In certain embodiments wherein the donor is not immunized to an antigen that is present in, or will be delivered to, the recipient, the delivery of CD4+ T-cell help is contingent upon donor CD4+ T-cell recognition of allogenic HLA Class II molecules on the recipient's cells. An example of an "ideal donor" for the purpose of exemplifying these embodiments of the present invention is then completely mismatched at HLA Class II alleles (in particular, HLA-DRB1, HLA-DQB1, and HLA-DPB1) and completely matched for Class I alleles (to maximize survival of donor cells in the recipient and minimize alloantibody formation against Class I molecules). Further, the ideal donor is completely mismatched with unshared HLAs of first-degree relatives of the recipient who are potential donors for allogenic stem cell transplantation.

In one embodiment, there is an allogenic lymphocyte composition derived from a peripheral blood cell composition of a human, allogenic donor for administration to a human recipient, the allogenic lymphocyte composition comprising a number of CD4+ T-cells and a number of natural killer cells from the peripheral blood cell composition of the donor, wherein (i) the donor comprises at least one human leukocyte antigen (HLA) Class II allele mismatch relative to the recipient in the donor versus the recipient direction and the HLA Class II allele mismatch is at a gene selected from the group consisting of HLA-DRB1, HLA-DQB1, and HLA-DPB1, (ii) the recipient does not have detectable antibodies reactive against human leukocyte antigens of the donor, (iii) the number of CD4+ T-cells in the allogenic lymphocyte composition differs from the number of CD4+ T-cells in the peripheral blood cell composition by less than about 50%, (including but not limited to less than about 50%, less than about 40%, preferably less than about 20%, more preferably less than about 10%). Further, "differs from the number of CD4+ T-cells in the peripheral blood cell composition by less than about 50%" means plus or minus less than 50% of the number of CD4+ T-cells in the peripheral blood cell composition. For example, if the number of CD4+ T-cells in the peripheral blood cell composition is $1\times10^5$ CD4+ cells, then "differs from the number of CD4+ T-cells in the peripheral blood cell composition by less than about 50%" means the number of CD4+ T-cells is between $1.5\times10^5$ and $0.5\times10^5$. In the composition, the number of donor CD4+ T-cells based on an ideal body weight (ideal body weight (IBW) is based on height. For men, IBW=50+2.3 kg/inch over 5 feet. For women, IBW=45.5+2.3 kg/inch over 5 feet) of the recipient in kilograms (kg) is between about $1\times10^5$ CD4+ T-cells/kg and about $1\times10^9$ CD4+ T-cells/kg (in a preferred embodiment, between about $1\times10^6$ CD4+ T-cells/kg and about $5\times10^8$ CD4+ T-cells/kg); (v) the number of natural killer cells in the allogenic lymphocyte composition is less than or equal to the number of natural killer cells in the peripheral blood cell composition, and (vi) the allogenic lymphocyte composition has at least one order of magnitude fewer CD8+ T-cells relative to the peripheral blood cell composition; with the proviso that the CD4+ T-cells of the allogenic lymphocyte composition are not activated ex vivo.

Also provided is a method of treating a disease or condition in a human subject, comprising administering a lymphoreductive (in some embodiments of this aspect of the present invention, it is desirable to provide a lymphoreductive non-lymphoablative treatment to promote the homeostatic expansion and differentiation of the administered lymphocyte composition; in other embodiments it is desirable that the treatment also be myeloreductive (i.e., inhibiting or depleting suppressive myeloid populations including myeloid-derived suppressor cells, tumor associate macrophage, and or N2 neutrophils) non-lymphoablative treatment to the subject to induce transient lymphopenia in the subject; and subsequently administering to the subject a first allogenic lymphocyte composition derived from a peripheral blood cell composition of a human, allogenic donor, the first allogenic lymphocyte composition comprising a number of CD4+ T-cells and a number of natural killer cells from the peripheral blood cell composition of the donor, wherein (i) the donor comprises at least one human leukocyte antigen (HLA) Class II allele mismatch relative to the subject in the donor versus the subject direction and the HLA Class II allele mismatch is at a gene selected from the group consisting of HLA-DRB1, HLA-DQB1, and HLA-DPB1, (ii) the subject does not have detectable antibodies reactive against human leukocyte antigens of the donor, (iii) the number of CD4+ T-cells in the first allogenic lymphocyte composition differs from the number of CD4+ T-cells in the peripheral blood cell composition by less than about 50%, (iv) the number of donor CD4+ T-cells based on an ideal body weight of the subject in kilograms (kg) is between about $1\times10^5$ CD4+ T-cells/kg and about $1\times10^9$ CD4+ T-cells/kg, (v) the number of natural killer cells in the first allogenic lymphocyte composition is less than or equal to the number of natural killer cells in the peripheral blood cell composition, and (vi) the first allogenic lymphocyte composition has at least one order of magnitude fewer CD8+ T-cells relative to the peripheral blood cell composition, with the proviso that the CD4+ T-cells of the first allogenic lymphocyte composition are not activated ex vivo.

While not wishing to be bound by a particular theory, the infused CD4+ cells provide signals to other cell types, predominately the subject's CD8+, macrophage, and/or antigen presenting cells that augment cytotoxic function of these cells in the subject (tolerized CD4+ of subject/exhausted CD8+ of subject); an example of treatment of a disease or condition by this method should be exemplified, at least treatment of myelodysplastic syndrome.

In one aspect, the lymphoreductive non-lymphoablative treatment comprises treating the subject with one or more cytoreductive agent selected from the group consisting of alkylating agents, alkyl sulphonates, nitrosoureas, triazenes, antimetabolites, pyrimidine analogs, purine analogs, vinca alkaloids, epipodophyllotoxins, antibiotics, dibromomannitol, deoxyspergualine, dimethyl myleran and thiotepa. In one aspect, the lymphoreductive non-lymphoablative treatment comprises treating the subject with an alkylating agent and the alkylating agent is cyclophosphamide. In one aspect, subsequent to administering the first allogenic lymphocyte composition to the subject, the method further comprises administration of an anti-tumor monoclonal antibody or anti-tumor monoclonal antibody/drug conjugate to the subject.

In one aspect, kits are provided for use in treating a disease or condition in a subject, the kit comprising: a lymphocyte composition as described herein wherein the subject is the human recipient; and a nanoparticle composition comprising nanoparticles comprising the antigen not present in the human recipient. In one aspect, the nanoparticles further comprise a cytokine, for example, an interleukin or an interferon. The cytokine can be an interleukin and is selected from the group consisting of IL-2, IL-7, IL-12, and IL-15. The cytokine is may be an interferon e.g., interferon gamma, interferon beta, interferon alpha, interferon, tau, interferon omega, and consensus interferon.

The nanoparticles may further comprise a compound selected from the group consisting of a chemokine, an imaging agent, a photo antenna molecule, a thermal antenna molecule, and a Toll-like receptor ligand, ligands that promote differentiation of CD4+ T-cells into Type I (e.g., IFN-gamma producing) CD4+ memory T-cells, ligands for receptors that induce activation of antigen presenting cells (e.g., anti-CD40 antibodies or aptamers). Further, the nanoparticles may include an agent that targets the nanoparticles to tumor cells or antigen-presenting cells.

In one aspect, method further comprises administration of the anti-tumor monoclonal antibody and the anti-tumor monoclonal antibody is selected from the group consisting of rituximab, cetuximab, trastuzumab, and pertuzumab. In one aspect, the invention comprises administration of the anti-tumor monoclonal antibody/drug conjugate and the anti-tumor monoclonal antibody/drug conjugate is selected from the group consisting of brentuximab vedotin, gemtuzumab ozogamicin, trastuzumab emtansine, inotuzumab ozogamicin, glembatumumab vedotin, lorvotuzumab mertansine, cantuzumab mertansine, and milatuzumab-doxorubicin. In some aspects, administration is first the allogenic lymphocyte composition and then administration of a chemotherapeutic agent to the subject. For example, the chemotherapeutic agent is selected from the group consisting of dasatinib, nilotinib, ponatinib, imatinib, lapatinib, and vismodegib.

In one aspect, subsequent to administering the first allogenic lymphocyte composition to the subject, the method further comprises administration of a monoclonal antibody/CD4+ T-cell epitope conjugate to the subject. In one aspect, subsequent to administering the first allogenic lymphocyte composition to the subject, the method further comprises administering a successive lymphoreductive non-lymphoablative treatment to the subject to induce transient lymphopenia in the subject; and subsequently administering to the subject a successive allogenic lymphocyte composition derived from an additional peripheral blood cell composition of an additional human, allogenic donor, the successive allogenic lymphocyte composition comprising a number of CD4+ T-cells and a number of natural killer cells from the additional peripheral blood cell composition of the additional donor, wherein (i) the additional donor comprises at least one human leukocyte antigen (HLA) Class II allele mismatch relative to the subject in the additional donor versus the subject direction and the HLA Class II allele mismatch is at a gene selected from the group consisting of HLA-DRB1, HLA-DQB1, and HLA-DPB1, (ii) the subject does not have detectable antibodies reactive against human leukocyte antigens of the additional donor, (iii) the number of CD4+ T-cells in the successive allogenic lymphocyte composition differs from the number of CD4+ T-cells in the additional peripheral blood cell composition by less than about 50%, (iv) the number of additional donor CD4+ T-cells based on an ideal body weight of the subject in kilograms (kg) is between about $1\times10^5$ CD4+ T-cells/kg and about $1\times10^9$ CD4+ T-cells/kg, (v) the number of natural killer cells in the successive allogenic lymphocyte composition is less than or equal to the number of natural killer cells in the additional peripheral blood cell composition, and (vi) the successive allogenic lymphocyte composition has at least one order of magnitude fewer CD8+ T-cells relative to the additional peripheral blood cell composition. With this method there is the proviso that the CD4+ T-cells of the successive allogenic lymphocyte composition are not activated ex vivo. Subsequent to administering the first allogenic lymphocyte composition to the subject, the method further comprises administration of an agent that blocks negative signaling in T-cells. The agent that blocks negative signaling in T-cell is selected from the group consisting of an anti-PD-1 antibody, ipilimumab, an anti-PD-L2 antibody, and a PD-1 fusion protein. The disease or condition is selected from the group consisting of a cancer, an autoimmune disorder, an organ transplantation, an allograft rejection, and a viral infection. For example, the disease or condition is a cancer and the cancer is myelodysplastic syndrome.

In one embodiment, the invention provides a method of making an allogenic lymphocyte composition for administration to a human recipient, comprising providing a peripheral blood cell composition from a human donor allogenic to the recipient, the peripheral blood cell composition comprising a number of CD4+ T-cells, a number of CD8+ T-cells, and a number of natural killer cells, wherein (i) the donor has CD4+ T-cell immunity against an antigen present in the recipient, (ii) the donor comprises at least one human leukocyte antigen (HLA) Class II allele match relative to the recipient and the HLA Class II allele match is at a gene selected from the group consisting of HLA-DRB1, HLA-DQB1, and HLA-DPB1, and (iii) the recipient does not have detectable antibodies reactive against human leukocyte antigens of the donor; and making the allogenic lymphocyte composition from the peripheral blood cell composition by reducing the number of CD8+ T-cells in the peripheral blood cell composition by at least one order of magnitude, wherein (a) the number of CD4+ T-cells in the allogenic lymphocyte composition differs from the number of CD4+ T-cells in the peripheral blood cell composition by less than about 50%, and (b) the number of natural killer cells in the allogenic lymphocyte composition is less than or equal to the number of natural killer cells in the peripheral blood cell composition, with the proviso that the CD4+ T-cells of the allogenic lymphocyte composition are not activated ex vivo.

In one aspect, the antigen present in the recipient is selected from the group consisting of a neoplastic antigen (neoplastic antigen is an antigen associated with a neoplasm where neoplasm is defined as any new and abnormal cellular growth, specifically one in which cellular replication is uncontrolled and progressive. Neoplasms may be benign, pre-malignant or malignant, and Cancers are malignant neoplasms. Thus all cancer antigens are neoplastic antigens but not all neoplastic antigens are cancer antigens. Neoplastic idiotype (Id) is a tumor-specific target, for example, in those B cell malignancies that express this molecule on their cell surface, for example, lymphoma or multiple myeloma, and include a viral antigen, a bacterial antigen, a fungal antigen, a parasitic antigen, and a non-human animal antigen.

In one aspect, a potential allogenic donor is selected from the one or more potential allogenic donor(s) based on minimizing mismatch between the potential allogenic donor and the recipient at the more than one HLA Class II alleles, and the potential allogenic donor is chosen as the donor. A potential allogenic donor is selected from the one or more potential allogenic donor(s) based on minimizing mismatch between the potential allogenic donor and the recipient at the one or more HLA Class I allele(s), and the potential allogenic donor is chosen as the donor.

In one aspect, the antigen present in the recipient against which the donor has immunity is a viral antigen and the viral antigen is selected from the group consisting of a human papillomavirus antigen, an Epstein Barr Virus antigen, a Kaposi's sarcoma-associated herpesvirus (KSHV) antigen, a Hepatitis A virus antigen, a Hepatitis B virus antigen, and a Hepatitis C virus antigen. For example, the viral antigen is a human papillomavirus antigen and the human papillomavirus antigen is an E6 or an E7 antigenic peptide. In one aspect, the number of CD4+ T-cells in the allogenic lymphocyte composition differs from the number of CD4+ T-cells in the peripheral blood cell composition by less than about 20%.

In one embodiment is provided an allogenic lymphocyte composition derived from a peripheral blood cell composition of a human, allogenic donor for administration to a human recipient, the allogenic lymphocyte composition comprising a number of CD4+ T-cells and a number of natural killer cells from the peripheral blood cell composition of the donor, wherein (i) the donor has CD4+ T-cell immunity against an antigen present in the recipient, (ii) the donor comprises at least one human leukocyte antigen (HLA) Class II allele match relative to the recipient and the HLA Class II allele match is at a gene selected from the group consisting of HLA-DRB1, HLA-DQB1, and HLA-DPB1, (iii) the recipient does not have detectable antibodies reactive against human leukocyte antigens of the donor, (iv) the number of CD4+ T-cells in the allogenic lymphocyte composition differs from the number of CD4+ T-cells in the peripheral blood cell composition by less than about 50%, (v) the number of donor CD4+ T-cells based on an ideal body weight of the recipient in kilograms (kg) is between about $1\times10^5$ CD4+ T-cells/kg and about $1\times10^9$ CD4+ T-cells/kg, (vi) the number of natural killer cells in the allogenic lymphocyte composition is less than or equal to the number of natural killer cells in the peripheral blood cell composition, and (vii) the allogenic lymphocyte composition has at least one order of magnitude fewer CD8+ T-cells relative to the peripheral blood cell composition; with the proviso that the CD4+ T-cells of the allogenic lymphocyte composition are not activated ex vivo.

The invention provides an allogenic lymphocyte composition derived from a peripheral blood cell composition of a human, allogenic donor for administration to a human recipient, the allogenic lymphocyte composition comprising a number of CD4+ T-cells and a number of natural killer cells from the peripheral blood cell composition of the donor, wherein (i) the donor has CD4+ T-cell immunity against an antigen not present in the recipient, (ii) the donor comprises at least one human leukocyte antigen (HLA) Class II allele match relative to the recipient and the HLA Class II allele match is at a gene selected from the group consisting of HLA-DRB1, HLA-DQB1, and HLA-DPB1, (iii) the recipient does not have detectable antibodies reactive against human leukocyte antigens of the donor, (iv) the number of CD4+ T-cells in the allogenic lymphocyte composition differs from the number of CD4+ T-cells in the peripheral blood cell composition by less than about 50%, (v) the number of donor CD4+ T-cells based on an ideal body weight of the recipient in kilograms (kg) is between about $1\times105$ CD4+ T-cells/kg and about $1\times109$ CD4+ T-cells/kg, (vi) the number of natural killer cells in the allogenic lymphocyte composition is less than or equal to the number of natural killer cells in the peripheral blood cell composition, and (vii) the allogenic lymphocyte composition has at least one order of magnitude fewer CD8+ T-cells relative to the peripheral blood cell composition; with the proviso that the CD4+ T-cells of the allogenic lymphocyte composition are not activated ex vivo.

The invention provides a method of treating a disease or condition in a human subject, comprising administering to the subject an allogenic lymphocyte composition derived from a peripheral blood cell composition of a human, allogenic donor, the allogenic lymphocyte composition comprising a number of CD4+ T-cells and a number of natural killer cells from the peripheral blood cell composition of the donor, wherein (i) the donor has CD4+ T-cell immunity against an antigen present in the subject, (ii) the donor comprises at least one human leukocyte antigen (HLA) Class II allele match relative to the subject and the HLA Class II allele match is at a gene selected from the group consisting of HLA-DRB1, HLA-DQB1, and HLA-DPB1, (iii) the subject does not have detectable antibodies reactive against human leukocyte antigens of the donor, (iv) the number of CD4+ T-cells in the allogenic lymphocyte composition differs from the number of CD4+ T-cells in the peripheral blood cell composition by less than about 50%, (v) the number of donor CD4+ T-cells based on an ideal body weight of the subject in kilograms (kg) is between about $1\times10^5$ CD4+ T-cells/kg and about $1\times10^9$ CD4+ T-cells/kg, (vi) the number of natural killer cells in the allogenic lymphocyte composition is less than or equal to the number of natural killer cells in the peripheral blood cell composition, and (vii) the allogenic lymphocyte composition has at least one order of magnitude fewer CD8+ T-cells relative to the peripheral blood cell composition; with the proviso that the CD4+ T-cells of the allogenic lymphocyte composition are not activated ex vivo.

The compositions and methods of the invention can be used against a broad range of cancers and tumor types, including but not limited to bladder cancer, brain cancer, breast cancer, colorectal cancer, cervical cancer, gastrointestinal cancer, genitourinary cancer, head and neck cancer, lung cancer, ovarian cancer, prostate cancer, renal cancer, skin cancer, and testicular cancer. More particularly, cancers that may be treated by the compositions and methods described herein include, but are not limited to, the following: cardiac cancers, including, for example sarcoma, e.g., angiosarcoma, fibrosarcoma, rhabdomyosarcoma, and liposarcoma; myxoma; rhabdomyoma; fibroma; lipoma and teratoma; lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma; gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma; genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and limphoma; liver cancers, including, for example, hepatoma, e.g., hepatocellular carcinoma; cholangiocarcinoma; hepatoblastoma; angiosarcoma; hepatocellular adenoma; and hemangioma; bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors; nervous system cancers, including, for example, cancers of the skull, e.g., osteoma, hemangioma, granuloma, xanthoma, and osteitis defoinians; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma; gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma; hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia; skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma. In certain embodiments, when the disease is cancer, it may include a lung cancer tumor, a breast cancer tumor, a prostate cancer tumor, a brain cancer tumor, or a skin cancer tumor for example.

The compositions of the invention can also be administered in combination with existing methods of treating cancers, for example by chemotherapy, irradiation, or surgery. Thus, there is further provided a method of treating cancer comprising administering an effective amount of an invention composition to an individual in need of such treatment, wherein an effective amount of at least one further cancer chemotherapeutic agent is administered to the individual. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

In methods of the invention described herein, optionally before administering to the subject the allogenic lymphocyte composition the method further comprises administering a treatment to deplete or inhibit myeloid-derived suppressor cells. The treatment to deplete or inhibit myeloid-derived suppressor cells may comprise administration of a drug selected from the group consisting of dasatinib, 5-fluorouracil, taxotere, clodronate, and gemcitabine for example. Optionally, before administering to the subject the allogenic lymphocyte composition the method further comprises administering a treatment to deplete or inhibit tumor associated macrophage cells. Optionally, before administering to the subject the allogenic lymphocyte composition the method further comprises administering a treatment to deplete regulatory T cells. The treatment to deplete regulatory T cells may include administration of a drug selected from the group consisting of cyclophosphamide, denileukin diftitox, and daclizumab.

In another embodiment, the invention provides a method of treating a disease or condition in a human subject comprising injecting a nanoparticle composition into a tumor (nanoparticles can be injected into or infused into the subject, wherein the nanoparticles further comprise a targeting agent, and the targeting agent binds to a target cell such as a dispersed/non-localized neoplasm (e.g., a lymphoma or leukemia) where direct injection to all possible sites is not practical or feasible), wherein the nanoparticle composition comprises nanoparticles comprising an antigen not present in the subject, thus introducing the antigen into the subject; administering to the subject an allogenic lymphocyte composition derived from a peripheral blood cell composition of a human, allogenic donor, the allogenic lymphocyte composition comprising a number of CD4+ T-cells and a number of natural killer cells from the peripheral blood cell composition of the donor, wherein (i) the donor has CD4+ T-cell immunity against the antigen, (ii) the donor comprises at least one human leukocyte antigen (HLA) Class II allele match relative to the subject and the HLA Class II allele match is at a gene selected from the group consisting of HLA-DRB1, HLA-DQB1, and HLA-DPB1, (iii) the subject does not have detectable antibodies reactive against human leukocyte antigens of the donor, (iv) the number of CD4+ T-cells in the allogenic lymphocyte composition differs from the number of CD4+ T-cells in the peripheral blood cell composition by less than about 50%, (v) the number of donor CD4+ T-cells based on an ideal body weight of the subject in kilograms (kg) is between about $1 \times 10^5$ CD4+ T-cells/kg and about $1 \times 10^9$ CD4+ T-cells/kg, (vi) the number of natural killer cells in the allogenic lymphocyte composition is less than or equal to the number of natural killer cells in the peripheral blood cell composition, and (vii) the allogenic lymphocyte composition has at least one order of magnitude fewer CD8+ T-cells relative to the peripheral blood cell composition; with the proviso that the CD4+ T-cells of the allogenic lymphocyte composition are not activated ex vivo. In one aspect, the antigen is a non-human animal antigen and the non-human animal antigen is a keyhole limpet hemocyanin antigen. In another aspect, the antigen is a viral antigen and viral antigen is selected from the group consisting of a human papillomavirus antigen, an Epstein Barr Virus antigen, a Kaposi's sarcoma-associated herpesvirus (KSHV) antigen, a Hepatitis A virus antigen, a Hepatitis B virus antigen, and a Hepatitis C virus antigen.

Compositions of the invention may be administered to the individual by a variety of routes, for example, orally, topically, parenterally, intravaginally, systemically, intramuscularly, rectally or intravenously. In certain embodiments, the composition is formulated with a pharmaceutical carrier. Preferably, the composition is administered intravenously.

In some embodiments, the composition is combined with other anti-viral or anti-cancer therapies, such as administration of an anti-viral or anti-cancer agent, radiation therapy, phototherapy or immunotherapy. The anti-viral or anti-cancer agent can be administered with an invention composition either in the same formulation or in separate formulations, to enhance treatment. In these embodiments, the composition and the other therapies can be administered at the same time (simultaneously) or at separate times (sequentially), provided that they are administered in such a manner and sufficiently close in time to have the desired effect.

The following examples are intended to illustrate but not limit the invention.

EXAMPLES

The myelodysplastic syndromes (MDS) are a diverse group of malignant stem cell disorders characterized by dysplastic and ineffective bone marrow production of blood cells and a variable risk of transformation to acute leukemia. These disorders may develop de novo or arise years after exposure to potentially mutagenic chemotherapy.

Approximately 12,000-20,000 new cases of MDS will be diagnosed in the United States this year with a median age of onset of between 60 and 72. Current treatment outcomes for the myelodysplastic syndromes have been disappointing. Age, performance status, and disease risk category, as determined by the International Prognostic Scoring System (IPSS), usually determine the choice of treatment modality. Patients <60 years of age, who have good or excellent performance status and who are in the IPSS intermediate-2 or high risk categories, would predominantly be considered for high intensity therapies, since these IPSS categories confer a median survival of 1.2 and 0.4 years, respectively. High-intensity therapies are defined as treatments requiring hospitalization, including intensive combination chemotherapy and hematopoetic cell transplantation.

Patients in the low or intermediate-1 category would generally be considered for low intensity therapies. These include treatments that can be administered in the outpatient clinic, such as hematopoetic growth factors, differentiation-inducing agents, biologic response modifiers, and low intensity chemotherapy. Patients with poor performance status would be considered for supportive care or low intensity therapies.

Example 1—IDE Device

The investigational agent to be used in this trial is the CliniMACS system with CliniMACS® CD8 reagent, a medical device that is used to enrich or deplete CD8+ T cells from human blood products. The CliniMACS® System intended for selection of CD8+ cells comprises four primary components: 1) CliniMACS® CD8 Reagent—colloidal super paramagnetic iron-dextran beads linked to a murine antibody against human CD8; 2) CliniMACSplus Instrument—a software controlled instrument that processes the blood sample (cell product); 3) CliniMACS® Tubing Set, (Standard or LS)—a single-use, sterile, disposable tubing set with two proprietary cell selection columns; and 4) CliniMACS® PBS/EDTA Buffer—a sterile, isotonic phosphate buffered, 1 mM EDTA, saline solution, used as external wash and transport fluid for the in vitro preparation of blood cells. The system utilizes magnetic cell sorting (MACS®), a powerful tool for the isolation of many cell types, to selectively enrich or deplete the cell population of interest. In this case, CD8+ T cells are labeled with a monoclonal antibody linked to super-paramagnetic particles and then are depleted from the blood product by passage through the CliniMACS system, which incorporates a strong permanent magnet and a separation column with a ferromagnic matrix to remove the labeled cells. It is worth nothing that the therapeutic agent in this trial, CD8+ T cell-depleted blood cells, comes out of the device and is not intended to contain any component of the device.

Example 2—Transiently Engrafting Donor Lymphocytes Induce Clinical Tumor Responses To date, only two therapies are capable of prolonging the survival of patients with MDS. The first, allogeneic BMT, has achieved some long term cures, as well as delay in disease progression. This therapy is only applicable to a small fraction of affected patients due to age, donor availability, and comorbidities. The second is the methyltransferase inhibitor, 5-azacitidine. This therapy has been shown to prolong median survival by 7 months compared to supportive care alone 10. Some patients with MDS respond to immunosuppressive regimens, such as cyclosporine, antithymocyte globulin (ATG) or steroids, with a sustained increase in blood counts. This finding is similar to aplastic anemia, where immunosuppression treats the autoimmune component leading to the cytopenias. The favorable results obtained with agents that specifically target the immune system suggest that MDS is a disease that is susceptible to immune modulation. One potential explanation for the benefit of ATG, cyclosporine, and steroids is that these drugs unmask the activity of an endogenous anti-tumor immune response by selectively inhibiting or killing lymphocytes that suppress anti-tumor immunity. Further potential evidence for the existence of a cryptic, endogenous immune response against MDS was seen in our trial of nonmyeloablative, partially HLA-mismatched (haploidentical) allogeneic bone marrow transplantation, in which five patients experienced disease responses despite graft rejection. All five patients had at least transient reductions in the percentage of bone marrow blasts, and three of five patients, each of whom was dependent upon red blood cell +/− platelet transfusions prior to transplantation, became transfusion independent. Table 1 demonstrates that, despite absence of donor cell engraftment on day 30 after BMT, at least three of five patients had a reduction of marrow blasts lasting at least six months after BMT.

TABLE 1

| Patient # (age in years) | Diagnosis | Donor chimerism (Day 30) | Blast % Pre-BMT | Blast % Post BMT (day) |
|---|---|---|---|---|
| 1 (39) | RAEB-t | 0 | 22 | 0 (181+) |
| 2 (62) | AA → RAEB | 0 | 15 | 0 (378) |
| 3 (62) | PCV → RAEB | 0 | 8 | 0 (342) |
| 4 (56) | RAEB | 0 | 5 | 2 |
| 5 (59) | RAEB-t | 0 | 20 | 4 (73) |
|  |  |  |  | 50 (78) |

Figure 3B:
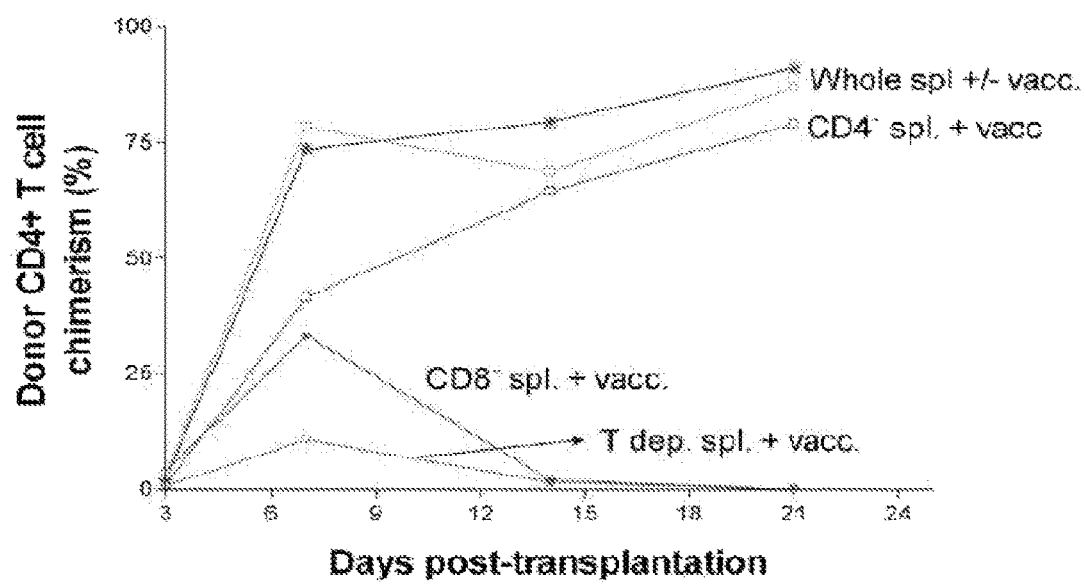
FIG. 3b shows a graph with donor CD4+ T cell chimerism and days post-transplantation.

FIG. 1 shows the hematocrits of the same five patients after BMT, with the jagged portions reflecting the effect of transfusion. Three of five patients became transfusion independent, with patient #1 remaining in morphologic and hematologic remission for at least three years. More interestingly, patient #2 demonstrated a delayed hematologic response, becoming transfusion independent four months after BMT and three months after documentation of graft rejection. In light of the sensitivity of MDS to immunotherapy, we raise the possibility that an endogenous (i.e. host-derived) anti-tumor immune response is reawakened by the immunological perturbation provided by the transiently engrafting donor lymphocytes. This postulated mechanism, the awakening of an endogenous anti-response following graft rejection, may also account for the induction of leukemia remission in patients receiving white blood cell transfusions after either no conditioning or only 100 cGy total body irradiation. Interestingly, in the latter study, three major clinical responses occurred in the absence of measurable donor chimerism. Clinical responses of both non-Hodgkin's and FIG. 2 shows a graph with percent survival and days after tumor inoculation to show non-engrafting DLI induces anti-tumor immunity. BALB/c×C57BL/6 F1 mice (H-2b/d; =10/group) were conditioned with Cy 200 mg/kg IP on day −1. On day 0, they received 106 A20 lymphoma cells IV+/−5×107 spleen cells from partially MHC-mismatched B6×C3H F1 donors (H-2b/k)+/−autologous tumor cell vaccine sc (106 irradiated A20+2×105 irr. B78H1-GM-CSF). Hodgkin's lymphoma despite the loss of donor chimerism following allogeneic BMT have also been described; in some of these cases, tumor regression following transiently engrafting donor lymphocyte infusions was observed. 24 While it is certainly possible that donor T cells induced an anti-leukemic effect before they were rejected, it is also possible that a transient GVH reaction broke functional tolerance to leukemia in host T cells. We have recently tested the hypothesis that transiently engrafting donor lymphocyte infusions (DLI) can induce anti-tumor immune responses from host T cells in a mouse model. BALB/c× C57BL/6 F1 mice were treated with Cy on day −1, and on day 0 they received 106 A20 lymphoma cells (of BALB/c origin) IV together with nothing, haploidentical DLI alone, autologous tumor cell vaccine alone, or DLI+vaccine. Compared to animals receiving either no treatment or vaccine alone after Cy conditioning, those that were conditioned with Cy and then treated with DLI alone or DLI+vaccine survived significantly longer, with apparent cure achieved in five and four animals, respectively (FIG. 2). None of the nine cured animals had any detectable donor chimerism when tested >100 days after DLI, suggesting that the donor T cells were rejected. These results demonstrated that the combination of Cy followed by partially MHC-mismatched DLI induced significant anti-tumor effects. In order to characterize the role of donor CD4+ versus CD8+ T cells in the antitumor effect, the experiment was repeated in recipients of Cy+vaccine+50 million mismatched spleen cells that were either untreated or depleted of CD4+ T cells, CD8+ T cells, or both. In this experiment, recipients of whole spleen DLI all died of GVHD before day 20 (FIG. 3). In contrast, mice that received vaccine plus CD8+ T cell depleted spleen cells lived significantly longer than mice receiving vaccine plus pan-T cell depleted spleen cells (p=0.04), indicating that depletion of CD8+ T cells abrogated lethal GVHD without abrogating anti-tumor immunity. In order to understand why depletion of CD8+ T cells from the allogeneic DLI abrogated GVHD, we studied the survival of donor cells in mice conditioned with Cy and then infused with mismatched spleen cells, either untreated or depleted of either or both T cell subsets. Interestingly, CD8+ T cell-depleted spleen cells engrafted only transiently, with donor CD4+ T cell chimerism peaking at 7 days after DLI and declining to undetectable levels by day 21 (below). In contrast, sustained engraftment of donor cells was seen in all mice receiving DLI containing CD8+ T cells, and most of these animals eventually died of GVHD. Taken together, the animal studies demonstrate that Cy followed by CD8+ T cell depleted DLI induces transient engraftment of donor cells and significant anti-tumor effects without inducing acute GVHD. More recently, we have found that depletion of host CD8+ T cells prior to "Cy+DLI" significantly diminishes the therapeutic effect, strongly implicating host CD8+ T cells as critical mediators of the anti-tumor effect.

Example 3—Clinical Experience with CD8+ T Cell Depleted Allogeneic Stem Cell or Lymphocyte Infusions There are no reports of patients treated with Cy followed by an infusion of CD8+ T cell depleted PBCs from haploidentical donors, so it is not possible to provide preliminary safety data. However, there have been reports of patients undergoing alloBMT who have received CD8+ T cell-depleted grafts or of patients in relapse after alloBMT who have received CD8+ T cell depleted PBMC infusions. The goal of CD8+ T cell depletion was to reduce the incidence of GVHD while preserving the anti-leukemia effect of the infusion. With regard to GVHD, the studies did not yield a conclusive answer, with some showing a possible benefit and others showing none. Interestingly, infusion of CD8+ T cell-depleted DLI induced the activation of endogenous CD8+ T cells, a finding that is consistent with the hypothesis that CD8+ T cell-depleted DLI can effectively awaken a host CD8+ T cell response against cancer.

The results of two other studies are germane to considerations of the safety of the proposed clinical trial. In the first study, patients with various hematologic malignancies received marrow from unrelated donors that were mismatched for either one HLA-DR allele or one HLA Class I (HLA-A or HLA-B) antigen. Patients received CD4+ T cell depleted grafts containing titrated doses of CD8+ T cells. The major finding relevant to the proposed study was that graft rejection occurred despite myeloablative conditioning in six of ten patients receiving grafts containing $<3.1 \times 10^6$ CD8+ T cells/kg of recipient body weight but in none of fifteen patients receiving $>3.1 \times 10^6$ CD8+ T cells/kg. Thus, even after myeloablative conditioning, CD8+ T cell depletion significantly increases the risk of graft rejection, which nullifies the risk of graft-induced aplasia and GVHD. In the second study patients received T cell-depleted, haploidentical peripheral blood stem cell (PBSC; n=15) or PBSC plus marrow grafts (n=28) containing a mean of $2.7 \times 10^4$ or $3.5 \times 10^4$ CD3+ T cells/kg, respectively, which translates to CD8+ T cell doses of approximately $1-1.5 \times 10^4$/kg. To facilitate engraftment in the face of T cell depletion, patients were conditioned intensively and received "mega-dose" stem cell grafts containing a mean of $14.0 \times 10^6$ or $10.6 \times 10^6$ CD34+ cells/kg for recipients of PBSC only versus PBSC plus marrow, respectively. In light of the low T cell content, no GVHD prophylaxis was administered. Engraftment occurred in all 43 patients, and no patient experienced acute or chronic GVHD as a result of the transplantation procedure. These data demonstrate that even when sustained engraftment occurs in patients receiving myeloablative conditioning, haploidentical grafts containing $<10^4$ CD8+ T cells/kg are unlikely to cause GVHD. Since the device usually achieves >2 log depletion of CD8+ T cells, the starting dose of CD8+ T cell depleted PBCs on the trial will likely contain fewer than $10^4$ CD8+ T cells/kg. It is likely, then, that no patients receiving this dose will engraft or experience GVHD, even if sustained engraftment occurs.

Example 4—CD8 Depletion Using the CliniMACS_System with CliniMACS-CD8 Reagent

Figure 4:
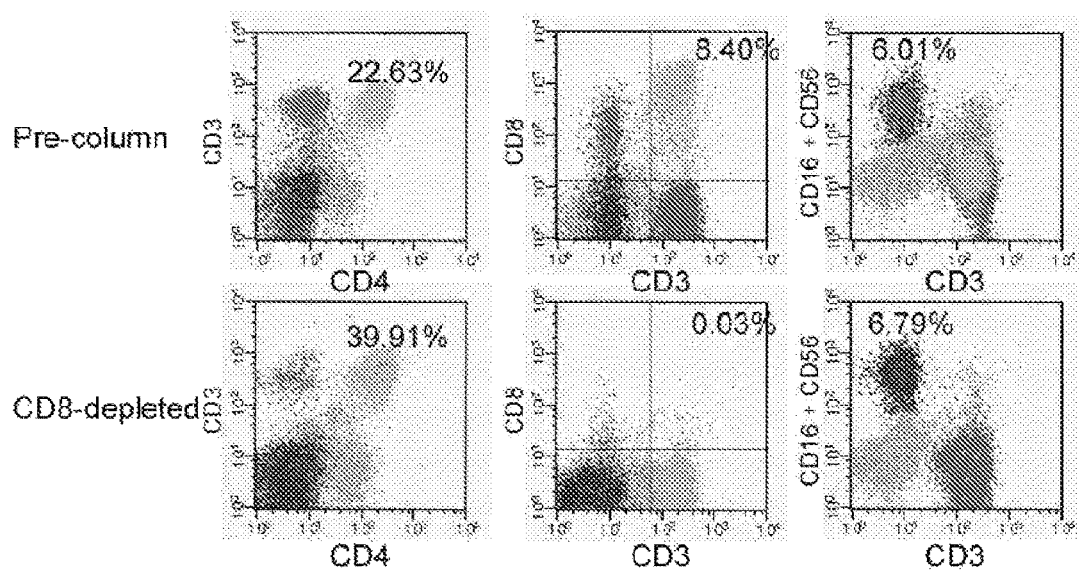
FIG. 4 shows validation runs for CD8 depletion using leukapheresis product and phlebotomy specimens (flow cytometry results).

For this trial, CD8+ T cells will be depleted using the CliniMACS_system with the CliniMACS_CD8 Reagent (Miltenyi Biotec, Woburn, Mass.), under an investigator-sponsored IDE. We have performed three validation runs, the first using a leukapheresis product, and the last two using phlebotomy specimens. Flow cytometry results from the last depletion are shown below, demonstrating excellent depletion of CD8+ T cells, from 8.40% to 0.03% of total cells, and a corresponding enrichment of CD4+ T cells and CD16+ or CD56+ NK cells (FIG. 4). Table 2 demonstrates all three products meet the protocol criterion of having a CD8+ T cell number that is <3.2% of the CD4+ T cell number. Had products #2 and #3 been used to deliver a dose of 106 CD4+ T cells/kg to a recipient with an ideal body weight of 70 kg, they would have contained $2.6 \times 103$ and $7.7 \times 102$ CD8+ T cells/kg IBW, respectively, doses that are well below the threshold for engraftment or GVHD induction. In comparison, the five patients who responded despite graft rejection received marrows containing a median of $1.43 \times 10^7$ CD4+ T cells/kg (range $0.84-3.14 \times 10^7$/kg) and $1.86 \times 10^7$ CD8+ T cells/kg (range $0.43-2.16 \times 10^7$/kg). Therefore, MDS patients are capable of rejecting haploidentical cell infusions containing this many T cells.

TABLE 2

CE8 Depleted Cell Product Validation Results

| | % CD4+ Cells | Total CD4+ Cells | % CD8+ Cells | Total CD8+ Cells | CD8+ Cells Log Depletion | Percent Viable | Sterility Result |
|---|---|---|---|---|---|---|---|
| Depletion #1 | 39.6% | $7.6 \times 10^8$ | 0.5% | $9.5 \times 10^6$ | 1.95 | 98% | Negative |
| #2 | 11.6% | $2.5 \times 10^8$ | 0.03% | $6.5 \times 10^5$ | 2.43 | 90% | Negative |
| #3 | 39.9% | $3.0 \times 10^8$ | 0.03% | $2.3 \times 10^5$ | 2.67 | 97% | Negative |

Example 5—Correlative Laboratory Studies to Predict Response to Therapy

In light of the potential toxicities of immunosuppressive therapies, such as antithymocyte globulin, in patients with MDS35, numerous investigators have endeavored to identify patient characteristics that correlate with response to therapy. Such characteristics that predict disease response include hypocellular marrow, abnormal T cell receptor repertoire by T cell receptor beta chain variable region CDR3 size by spectratype analysis, presence of cells with a phenotype characteristic of paroxysmal nocturnal hemoglobinuria (PNH), expression of HLADR15, trisomy 8, younger age, and shorter transfusion history. A major goal of this trial is to determine whether characteristics that predict response to immunosuppressive therapy can also predict response to Cy+CD8+ T cell-depleted haploidentical DLI. Patients entered onto this trial will have examination of T cell receptor spectratype both before and after therapy. Cytogenetics and HLA typing will be performed routinely on all patients.

Recent studies have uncovered a role for donor natural killer cell alloreactivity in preventing relapse of acute leukemia after haploidentical stem cell transplantation 36-38. More recently, alloreactive natural killer cells of donor origin have been found to prevent relapse of AML and MDS after HLA-identical stem cell transplantation 39. These results underscore the need to characterize the expressed repertoire of killer immunoglobulin-like receptors, or KIRs, on donor NK cells using both molecular and flow cytometric methods so as to identify donors expressing KIRs whose HLA ligands are missing on recipient cells. These studies will be performed retrospectively in the Immunogenetics Laboratory and the results correlated with response to therapy.

Example 6—Rationale for the Proposed Trial Design

This is a standard phase I/II trial design that seeks to determine, in the phase I portion of the trial, the maximally tolerated dose (MTD) of CD8+ T cell-depleted haploidentical peripheral blood cells (CD8− PBCs) when infused after cyclophosphamide (Cy), and then to estimate, in the phase II portion of the trial, the efficacy of treatment with Cy plus the MTD of CD8− PBCs. High dose Cy (>100 mg/kg) has been used extensively as part of transplantation conditioning for patients with hematologic malignancies, and its safety is well-documented in this population, including elderly patients (ages 55-66) with myelodysplastic syndrome. The most serious risks of treatment, because they have the potential to cause death, are prolonged aplasia and graft-versus host disease, both of which require sustained engraftment of the donor cells. The choice of the initial cell dose, $10^5$ CD4+ T cells/kg and <$3.2 \times 10^3$ CD8+ T cells/kg, was based solely upon safety considerations. Specifically, grafts containing <104 CD8+ T cells/kg do not cause severe GVHD, even among patients receiving lethal conditioning and no pharmacologic immunosuppression after transplantation. Moreover, partial depletion of CD8+ T cells from standard marrow grafts significantly increases the risk of graft rejection 33, which is the desired outcome of treatment in this trial. For these reasons, it is felt that a DLI product containing <104 CD8+ T cells/kg is unlikely to cause serious adverse events.

Experience with haploidentical DLI, without CD8+ T-cell depletion, has been recently published. In a phase I/II trial, 41 patients with relapsed/refractory malignancies received nonablative conditioning with 100 cGy total body irradiation, followed by infusion of $1 \times 10^6$ to $2 \times 10^8$ haploidentical CD3+ cells/kg, with 29 patients receiving the highest dose. Objective responses were achieved at the higher dose levels. Notably, $1 \times 10^8$ CD3+ cells/dose was the minimum dose associated with response (25% response rate, or 2 of 8 patients), with $2 \times 10^8$ CD3+ cells/dose (the highest evaluated) associated with the greatest response rate (nearly 50%, in 10 of 21 patients). As proof of principle, all responses occurred in the absence of sustained donor chimerism. In the highest dose cohort, transient donor chimerism was seen but disappeared by 2 weeks in most patients, with one of two patients who converted to full donor chimerism developing severe acute GVHD (steroid responsive, with subsequent development of fatal sepsis). An acute clinical syndrome termed "haplo immunostorm" likely secondary to cytokine flux (characterized by 1 or more of the following: fever, malaise, LFT abnormalities, rash and diarrhea) was seen commonly at the higher dose levels and was exquisitely responsive to steroids. This study demonstrated the biological activity and manageable safety profile of this approach. The minimum CD3+ T-cell dose (not CD8+ depleted) required for response in that study was $1 \times 10^8$ cells/kg.

Example 7—Patent Selection

Patients must have pathologically confirmed: Myelodysplastic syndrome (MDS), IPSS score of Int-2 or high (see Appendix A for IPSS scoring system). Patients must have failed or be ineligible or intolerant of treatment with 5-azacitidine.

Example 8—Treatment Plan

All patients will require documentation of a detailed history and physical examination and standard evaluation of cardiac, liver and renal function, as designated in section 10. All patients will undergo a bone marrow aspirate and biopsy for morphological, cytogenetic (if applicable) and flow cytometric (if applicable) evaluation no more than one month prior to registration on protocol, along with other standard disease evaluations (e.g., CT of chest, abdomen, pelvis) where applicable.
Pre-Treatment Evaluation Cyclophosphamide will be administered as an iv infusion over 1-2 hr, (depending on volume) on days −2 and −1. The dose of cyclophosphamide is 50 mg/kg/day. Dose is calculated based on the adjusted ideal body weight or actual body weight whichever is less. Body weight and height are measured directly. An approximate weight for height would be calculated from a standard table or equations that reflect ideal "values".
Cyclophosphamide and Pre-DLI Regimen Patients will be instructed to increase fluids overnight before cyclophosphamide administration. Hydration with normal saline at 3 cc/kg/hr iv will be started 2 hr prior to cyclophosphamide, then the rate will be reduced to 2 cc/kg/hr for 1 hr precyclophosphamide and continued for 8 hr post-cyclophosphamide. Mesna will be given in divided doses iv 30 min pre- and at 3, 6, and 8 hr post cyclophosphamide.

Mesna dose will be based on the cyclophosphamide dose being given. The total daily dose of mesna is equal to 80% of the total daily dose of cyclophosphamide.

Prophylactic anti-microbial therapy will be started on Day 0 and will follow institutional practice.

Antifungal prophylaxis will be administered as follows: Fluconazole 400 mg po or IV qd, beginning Day 0 and continuing until the ANC is >500 for 3 consecutive days (or for 2 consecutive measurements over a 3 day period). Another appropriate prophylactic antifungal agent may be substituted. *Pneumocystis carinii* pneumonia (PCP) prophylaxis will start on Day 0 and should continue until Day 60. Patients intolerant of trimethoprim/sulfamethoxazole (Bactrim) will receive either dapsone or pentamidine as PCP prophylaxis. Viral prophylaxis will consist of valacyclovir or acyclovir from Day 0 to Day 60. An oral quinolone (e.g., moxifloxacin or norfloxacin) will be administered according to institutional preference until the ANC is >500 for 3 consecutive days (or for 2 consecutive measurements over a 3 day period) following DLI.

All patients will receive infusion of haploidentical PBCs depleted of CD8+ T cells using the CliniMACS® system with CliniMACS® CD8 reagent. The numbering of the dose levels is from the lowest to the highest cell dose. The first cohort of patients (dose level 1) will receive Cy plus CD8+ T cell-depleted haploidentical PBCs (CD8– PBCs) containing an intended dose of 1×105 CD4+ T cells/kg of recipient IBW. If criteria for dose escalation are met, patients on dose level 2, 2b, 3, or 4 will receive CD8– PBCs containing an intended dose of $1\times10^6$, 3×106, $1\times10^7$, or $5\times10^7$ CD4+ T cells/kg, respectively.

DLI Dose Calculation

The formula for calculating the volume of final (CD8-depleted) product that will deliver the intended dose of CD4+ T cells is as follows: Intended volume (ml)=Intended CD4+ T cell dose (cells/kg)×Recipient IBW* (kg)/CD4+ T cell concentration (cells/ml) *Note—If actual weight<ideal, use actual weight.

However, the total number of CD8+ T cells that are infused may not exceed 3.2% of the intended number of CD4+ T cells to be infused (the numerator of the equation above). If the ratio of CD4+/CD8+ cells in the depleted product is less than 31.25 (=1/0.032), then the volume of the product to be infused will be determined by the following formula: If CD4/CD8 ratio of final product <31.25, then: Infused volume (ml)=Intended volume×(CD4/CD8 ratio)/31.25 If the ratio of CD4+/CD8+ cells in the depleted product is equal to or greater than 31.25, then the volume of the product to be infused is the intended volume (formula 1): If CD4/CD8 ratio of final product >31.25, then: Infused volume (ml) =Intended volume Transfusion Support Platelet and packed red cell transfusions will be given per current institutional recommendations.

Example 9—Duration of Therapy

Patients are eligible for only one lymphocyte infusion. This restriction is in place because rejection of the infused lymphocytes is expected to induce anamnestic immunity to cells of the donor or even to other close relatives. Patient's peripheral blood will be obtained on day 60 and tested for the presence of human anti-mouse antibody (HAMA) and for cytotoxic antibodies against donor cells.

Duration of Follow Up

Patients will be followed for a minimum of 60 days after DLI, and then until death or disease progression, whichever occurs first. Patients removed from study for unacceptable adverse events or who develop treatment-related adverse events will be followed until resolution or stabilization of the adverse event.

Post DLI Monitoring:

Patients remaining on study will have blood drawn on days 14, 28, and 60, and six months after DLI. A CBC with manual differential will be obtained with these blood draws. Lymphocyte subsets, including the percentage of cells expressing CD4 or CD8, will be analyzed by flow cytometry. After day 60, the patient will have monthly complete blood counts with white blood cell differential as long as there is no documented disease progression, until 6 months after DLI.

Disease Assessment.

In addition to disease assessments specified above, results of additional disease assessments performed as standard of care will be collected for study purposes until death or disease progression, whichever occurs first.

Example 10—Dosing Delays/Dose Modification

Cyclophosphamide dose will not be modified. DLI dose will be modified in the event of excessive content of CD8+ T cells.

Adverse Events: List and Reporting Requirements

The following information shall be collected on all patients with acute GVHD: Date of onset (defined as the date of first biopsy confirming GVHD) GVHD evaluation form at the time of onset, weekly until GVHD resolves, and Day 60 Initial overall clinical grade Maximum overall clinical grade Date of onset of grade III-IV acute GVHD, if any The occurrence and severity of acute and chronic GVHD after Day 60 will be captured at the patient's six month evaluation.

All instances of grade II-IV acute GVHD will be captured as adverse events. Grade III-IV GVHD will be reported as a serious adverse event.

DLI-induced aplasia is defined as neutropenia (absolute neutrophil count <500/ml) with any evidence of donor chimerism on day 60 or later. All cases of DLI induced aplasia will be reported as serious adverse events.

Example 11—Pharmaceutical Information

Cyclophosphamide (Cytoxan®)

Cyclophosphamide is commercially available. Cyclophosphamide is an alkylating agent which prevents cell division primarily by cross-linking DNA strands. Cyclophosphamide is cell cycle non-specific. Cyclophosphamide for injection is available in 2000 mg vials which are reconstituted with 100 ml sterile water for injection. The concentration of the reconstituted product is 20 mg/ml. The calculated dose will be diluted further in 250-500 ml of Dextrose 5% in water. Each dose will be infused over 1-2 hr (depending on the total volume).

Clinical toxicities of cyclophosphamide include alopecia, nausea and vomiting, headache and dizziness, hemorrhagic cystitis, cardiotoxicity, immunosuppression, myclosuppression, pulmonary fibrosis, increased hepatic enzymes and syndrome of inappropriate anti-diuretic hormone (SIADH). Cyclophosphamide will be dispensed by the Oncology Pharmacy and is produced by Mead Johnson Pharmaceuticals.

Mesna (sodium-2-mercapto ethane sulphonate)

Mesna is a prophylactic agent used to prevent hemorrhagic cystitis induced by the oxasophosphorines (cyclophosphamide and ifosphamide). It has no intrinsic cytotoxicity and no antagonistic effects on chemotherapy. Mesna binds with acrolein, the urotoxic metabolite produced by the oxasophosphorines, to produce a non-toxic thioether and slows the rate of acrolein formation by combining with 4-hydroxy metabolites of oxasophosphorines.

Mesna is available in 200 mg, 400 mg and 1000 mg vials containing a 100 mg/ml solution. Each dose of mesna will be diluted further in 50 ml of normal saline to be infused over 15 min. Mesna dose will be based on the cyclophosphamide dose being given. The total daily dose of mesna is equal to 80% of the total daily dose of cyclophosphamide. At the doses used for uroprotection mesna is virtually non-toxic. However, adverse effects which may be attributable to mesna include nausea and vomiting, diarrhea, abdominal pain, altered taste, rash, urticaria, headache, joint or limb pain, hypotension and fatigue.

CBER IDE Device

Donors will have their blood collected via peripheral whole blood collection (450 ml into CPDA-1) or a leukapheresis procedure to collect peripheral white blood cells under steady state conditions (without mobilization). Each leukapheresis collection will be performed on a continuous flow cell separator (COBE Spectra, Gambro) using institutional standard operating procedures for lymphocyte collection. The method of blood donation, phlebotomy versus leukapheresis, will be determined by obtaining a peripheral blood absolute CD4+ T cell count within 30 days prior to donation and by estimating the volume of blood required to obtain the targeted CD4+ T cell dose. Since the normal range of peripheral blood CD4+ T cell counts is $0.5-1.5\times10^6$/ml, it is likely that simple phlebotomy will be sufficient for dose levels 1-2, pheresis may be required for levels 2b but leukapheresis will be required for dose level 3 and 4.

Based upon extensive prior experience, a 4 hour leukapheresis procedure should be sufficient to obtain $5\times10^7$ CD4+ T cells/kg of recipient IBW. Target collections will be at least 30% more than the desired dose to accommodate for cell loss during the depletion process.

The product will undergo CD8 depletion in the Graft Engineering Laboratory. All standard operating procedures will be followed. The product will be analyzed for nucleated cell count, CD3, CD4, CD8, CD16, and CD56. The product will be stored overnight and CD8 depletion will take place on the CliniMACS® Selection System (Miltenyi Biotec, Auburn, Calif.). Prior to CD8 depletion, whole blood products will initially be processed to prepare a buffy coat concentrate and for major ABO incompatible donor/recipient pairs the buffy coat concentrate will be further processed using lymphocyte separation medium to remove contaminating red blood cells. Processed whole blood products or apheresis products are then concentrated and resuspended in PBS/EDTA supplemented with 0.5% human serum albumin. Murine monoclonal CD8 antibody, conjugated to iron-dextran super-paramagnetic particles is added and incubated at room temperature for 30 minutes. One vial of antibody will be used to treat up to $40\times10^9$ total white blood cells and up to $4\times10^9$ CD8+ cells. Excess antibody will be removed by washing 1 time and the product volume will be adjusted to 100 ml with PBS/EDTA with albumin. It is then connected to the CliniMACS Selection System using a sterile disposable tubing set. The run is initiated by a pre-set computer program which controls (i) the flow of antibody-treated cells, (ii) washing that removes residual unbound cells, (iii) removal of the magnetic field around the column to release selected cells, and (iv) the final collection of CD8 depleted cells into a bag. The entire process takes approximately 2-6 hours from completion of initial product concentration. The subsequent product will be analyzed for cell count, viability, CD3, CD4, CD8, CD16, and CD56 content. The CD4 concentration will be used to calculate the patient dose. The calculated volume will be removed and prepared for infusion according to institutional standard operating procedures.

Correlative/Special Studies

Phenotypic Immune Reconstitution

Peripheral blood concentrations of lymphocyte subsets including CD4+ and CD8+ T cells will be determined using the absolute lymphocyte count and flow cytometry on days 14, 28, 60, and 6 months after DLI.

Analysis of Host CD8+ T Cell Repertoire Diversity by Spectratype Analysis. Recent studies indicate that the diversity of the T cell repertoire can be assessed by T cell receptor V_region spectratyping, which evaluates the CDR3/diversity/joining regions (Vβ-D-J-Cβ) of cells expressing a given V_gene. This region confers specificity of the T cell receptor. Immunoscoping or V_spectratyping is remarkably useful for evaluating anti-tumor immune responses following therapy and immune reconstitution following bone marrow transplantation 49. Moreover, spectratype analysis of MDS patients before and after immunosuppressive therapy has revealed skewing of the T cell repertoire that normalizes with a response to treatment. We therefore hypothesize that patients with MDS and possibly CMML will have skewed T cell repertoires prior to treatment, that the DLI will initially induce a population of alloreactive T cells, and that responders will eventually acquire a normal T cell repertoire as revealed by spectratype analysis. Pre-treatment CD8+ T cells will be obtained from patient peripheral blood mononuclear cells (PBMCs). To identify patient anti-donor reactive T cells, pre-treatment PBMCs from the patient will be cultured for seven days with irradiated donor PBMCs prior to cell sorting. The culture period allow for the clonal expansion of patient anti-donor T cells. PBMCs will also be collected and CD8+ T cells will be purified on days 14, 28, 60, and at six months.

Those of skill in the art should, in light of the present disclosure, appreciate that many changes can be made in the specific embodiments which are disclosed and still obtain a like or similar result without departing from the spirit and scope of the invention. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Accordingly, the invention is limited only by the following claims.

What is claimed is:

1. A method of treating a disease or condition in a human subject, comprising:

administering a lymphoreductive non-lymphoablative treatment to the subject to induce transient lymphopenia in the subject; and subsequently administering to the subject a first allogenic lymphocyte composition derived from a peripheral blood cell composition of a human, allogenic donor, the first allogenic lymphocyte composition comprising a number of CD4+ T-cells and a number of natural killer cells from the peripheral blood cell composition of the donor, wherein the number of CD4+ T-cells in the first allogenic lymphocyte composition differs from the number of CD4+ T-cells in the peripheral blood cell composition by less than about 50%; the number of natural killer cells in the first allogenic lymphocyte composition is less than or equal to the number of natural killer cells in the peripheral blood cell composition, and the first allogenic lymphocyte composition has at least one order of magnitude fewer CD8+ T-cells relative to the peripheral blood cell composition, wherein (i) the donor comprises at least one human leukocyte antigen (HLA) Class II allele mismatch relative to the subject in the donor versus the subject direction and the HLA Class II allele mismatch is at a gene selected from the group consisting of HLA-DRB1, HLA-DQB1, and HLA-DPB1, (ii) the subject does not have detectable antibodies reactive against human leukocyte antigens of the donor, with the proviso that the CD4+ T-cells of the first allogenic lymphocyte composition are not activated ex vivo, and wherein the disease or condition is selected from the group consisting of a neoplasm and cancer.

2. The method of claim 1, wherein the lymphoreductive non-lymphoablative treatment comprises treating the subject with one or more cytoreductive agent selected from the group consisting of alkylating agents, alkyl sulphonates, nitrosoureas, triazenes, antimetabolites, pyrimidine analogs, purine analogs, vinca alkaloids, epipodophyllotoxins, antibiotics, dibromomannitol, deoxyspergualine, dimethyl myleran and thiotepa.

3. The method of claim 1, wherein subsequent to administering the first allogenic lymphocyte composition to the subject, the method further comprises administration of an anti-tumor monoclonal antibody or anti-tumor monoclonal antibody/drug conjugate to the subject.

4. The method of claim 1, wherein subsequent to administering the first allogenic lymphocyte composition to the subject, the method further comprises administering a successive lymphoreductive non-lymphoablative treatment to the subject to induce transient lymphopenia in the subject; and subsequently administering to the subject a successive allogenic lymphocyte composition derived from an additional peripheral blood cell composition of an additional human, allogenic donor, the successive allogenic lymphocyte composition comprising a number of CD4+ T-cells and a number of natural killer cells from the additional peripheral blood cell composition of the additional donor, wherein (i) the additional donor comprises at least one human leukocyte antigen (HLA) Class II allele mismatch relative to the subject in the additional donor versus the subject direction and the HLA Class II allele mismatch is at a gene selected from the group consisting of HLA-DRB1, HLA-DQB1, and HLA-DPB1, (ii) the subject does not have detectable antibodies reactive against human leukocyte antigens of the additional donor, (iii) the number of CD4+ T-cells in the successive allogenic lymphocyte composition differs from the number of CD4+ T-cells in the additional peripheral blood cell composition by less than about 50%, (iv) the number of additional donor CD4+ T-cells based on an ideal body weight of the subject in kilograms (kg) is between about $1\times10^5$ CD4+ T-cells/kg and about $1\times10^9$ CD4+ T-cells/kg, (v) the number of natural killer cells in the successive allogenic lymphocyte composition is less than or equal to the number of natural killer cells in the additional peripheral blood cell composition, and (vi) the successive allogenic lymphocyte composition has at least one order of magnitude fewer CD8+ T-cells relative to the additional peripheral blood cell composition.

5. The method of claim 4, with the proviso that the CD4+ T-cells of the successive allogenic lymphocyte composition are not activated ex vivo.

6. The method of claim 1, wherein the disease or condition is a cancer and the cancer is myelodysplastic syndrome.

7. The method of claim 1, wherein (iii) the number of donor CD4+ T-cells based on an ideal body weight of the subject in kilograms (kg) is between about $1\times10^5$ CD4+ T-cells/kg and about $1\times10^9$ CD4+ T-cells/kg.

8. The method of claim 2, wherein the lymphoreductive non-lymphoablative treatment comprises treating the subject with an alkylating agent and the alkylating agent is cyclophosphamide.

9. The method of claim 3, wherein the method further comprises administration of the anti-tumor monoclonal antibody and the anti-tumor monoclonal antibody is selected from the group consisting of rituximab, cetuximab, trastuzumab, bevacizumab, panitumumab and pertuzumab.

10. The method of claim 3, wherein the method further comprises administration of the anti-tumor monoclonal antibody/drug conjugate and the anti-tumor monoclonal antibody/drug conjugate is selected from the group consisting of brentuximab vedotin, gemtuzumab ozogamicin, trastuzumab emtansine, inotuzumab ozogamicin, glembatumumab vedotin, lorvotuzumab mertansine, cantuzumab mertansine, and milatuzumab-doxorubicin.

11. The method of claim 1, wherein subsequent to administering the first allogenic lymphocyte composition to the subject, the method further comprises administration of a chemotherapeutic agent to the subject.

12. The method of claim 11, wherein the chemotherapeutic agent is selected from the group consisting of dasatinib, nilotinib, ponatinib, imatinib, lapatinib, and vismodegib.

13. The method of claim 1, wherein subsequent to administering the first allogenic lymphocyte composition to the subject, the method further comprises administration of a monoclonal antibody/CD4+ T-cell epitope conjugate to the subject.

14. The method of claim 1, wherein subsequent to administering the first allogenic lymphocyte composition to the subject, the method further comprises administration of an agent that blocks negative signaling in T-cells.

15. The method of claim 14, wherein the agent that blocks negative signaling in T-cell is selected from the group consisting of an anti-PD-1 antibody, ipilimumab, an anti-PD-L2 antibody, and a PD-1 fusion protein.

* * * * *